(12) United States Patent
Reverdy et al.

(10) Patent No.: US 12,215,069 B2
(45) Date of Patent: Feb. 4, 2025

(54) SIRTUIN MODULATING COMPOUNDS AND APPLICATIONS THEREOF

(71) Applicant: Codagen Biosciences, Inc., Mt. Laurel, NJ (US)

(72) Inventors: Célina Reverdy, Chilly Mazarin (FR); Gaetan Gitton, Mt. Laurel, NJ (US); Xiangying Guan, Mt. Laurel, NJ (US); Indranil Adhya, Mt. Laurel, NJ (US); Rama Krishna Dumpati, Mt. Laurel, NJ (US); Samir Roy, Mt. Laurel, NJ (US); Santu Chall, Mt. Laurel, NJ (US); Anisha Ghosh, Mt. Laurel, NJ (US); Gauthier Errasti, Orsay (FR); Thomas Delacroix, Mennecy (FR); Raj Chakrabarti, Moorestown, NJ (US)

(73) Assignee: CODAGEN BIOSCIENCES, INC., Mt. Laurel, NJ (US)

( * ) Notice: Subject to any disclaimer, the term of this patent is extended or adjusted under 35 U.S.C. 154(b) by 0 days.

(21) Appl. No.: 18/421,117

(22) Filed: Jan. 24, 2024

(65) Prior Publication Data
US 2024/0228432 A1    Jul. 11, 2024

Related U.S. Application Data

(62) Division of application No. 18/090,953, filed on Dec. 29, 2022, now Pat. No. 12,012,370.

(51) Int. Cl.
| | | |
|---|---|---|
| *C07C 235/40* | (2006.01) | |
| *C07D 209/82* | (2006.01) | |
| *C07D 213/56* | (2006.01) | |
| *C07D 215/50* | (2006.01) | |
| *C07D 223/28* | (2006.01) | |
| *C07D 295/155* | (2006.01) | |
| *C07D 333/80* | (2006.01) | |

(52) U.S. Cl.
CPC .......... *C07C 235/40* (2013.01); *C07D 209/82* (2013.01); *C07D 213/56* (2013.01); *C07D 215/50* (2013.01); *C07D 223/28* (2013.01); *C07D 295/155* (2013.01); *C07D 333/80* (2013.01)

(58) Field of Classification Search
CPC .................................... C07C 235/40
See application file for complete search history.

(56) References Cited

U.S. PATENT DOCUMENTS 8,044,198 B2 * 10/2011 Nunes ............... A61P 19/00
544/235

* cited by examiner

*Primary Examiner* — Golam M Shameem
(74) *Attorney, Agent, or Firm* — J. Clinton Wimbish; Maynard Nexsen PC

(57) ABSTRACT

In one aspect, compounds modulating sirtuin activity are described herein. Sirtuin modulation by compounds described herein includes sirtuin activation and sirtuin inhibition. Modulation of sirtuin activity includes sirtuin activation and/or sirtuin inhibition. In some embodiments, a sirtuin modulating compound and/or salt thereof is of Formula I described herein.

5 Claims, 58 Drawing Sheets

SIRTUIN MODULATING COMPOUNDS AND APPLICATIONS THEREOF

RELATED APPLICATION DATA

The present invention is a divisional application of U.S. patent application Ser. No. 18/090,953 filed Dec. 29, 2022.

FIELD

The present application addresses compounds exhibiting sirtuin modulating functionality and, in particular, to compounds for the modulation of SIRT3.

BACKGROUND

Sirtuins are a family of proteins known as Class III histone deacetylases. These NAD$^+$ dependent enzymes are highly conserved in mammals throughout evolution. They deacetylate various substrates and control pivotal processes in the cells from genomic integration to stress response and metabolism. There are 7 sirtuins in mammals that differ in their localization and function. Sirt1, 6 and 7 are in the nucleus and are involved in DNA maintenance and transcription, while Sirt2, located in the cytoplasm, contributes to tubulin polymerization. Sirt3, 4 and 5 are localized in the mitochondria out of which Sirt3 is the prime deacetylase in regulating metabolism and promoting adaptation to nutrient starvation. Sirt3 is a key regulator of mitochondrial metabolism including the tricarboxylic acid cycle (TCA), urea cycle, amino acid metabolism, electron transport chain or oxidative phosphorylation, ROS detoxification and mitochondrial unfolded protein response. Sirt3 is predominantly expressed in tissues rich in mitochondria such as kidney, heart, brain and liver tissue. Thus, Sirt3 activity in these tissues is crucial to maintain mitochondrial function. Sirt3 has been shown to regulate aging, neurodegeneration, liver, kidney, heart diseases and other metabolic diseases. Due to its diverse role in the biological functioning of the cells, it has emerged to be a promising therapeutic target and several studies over the years have reported some activators or inhibitors of Sirt3. The catalytic core of Sirt3 is highly conserved and consists of a large Rossmann-fold domain and a smaller zinc binding domain.

Sirt3 is a NAD$^+$ dependent lysine deacylase, requiring the cofactor NAD$^+$ to remove acyl groups from lysine groups of its substrates. The acetylated substrate and the NAD$^+$ cofactor bind in between the two domains forming a stabilized cofactor binding loop. In the active conformation, the NAD$^+$ is buried in the C-pocket facilitating nicotinamide (NAM) release and an alkylimidate intermediate formation. Further hydrolysis of the intermediate yields the deacetylated peptide product and 2'-O-acetyl-ADP-ribose (OAADPr).

The most widely known Sirt3 activator, Honokiol (HKL), has shown some therapeutic effects in heart diseases, cancer and metabolic diseases but the mechanism remains to be elucidated. Currently known Sirt3 inhibitors such as 3-TYP are used only as probes without therapeutic application.

SUMMARY

In one aspect, compounds modulating sirtuin activity are described herein. Sirtuin modulation by compounds described herein includes sirtuin activation and sirtuin inhibition. Modulation of sirtuin activity includes sirtuin activation and/or sirtuin inhibition. In some embodiments, a sirtuin modulating compound and/or salt thereof is of Formula I:

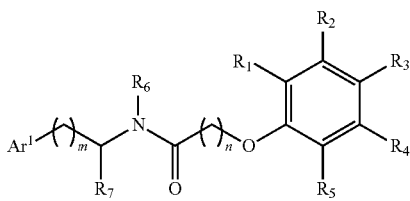

wherein Ar$^1$ is aryl or heteroaryl, R$_1$-R$_7$ are independently selected from the group consisting of hydrogen, alkyl, alkenyl, heteroalkyl, cycloalkyl, heterocycloalkyl, —C(O)R$_8$, alkoxy, halo, nitryl (—NO$_2$), and hydroxy, wherein the Ar$^1$, alkyl, alkenyl, heteroalkyl, cycloalkyl, heterocycloalkyl, aryl, heteroaryl are optionally substituted with one or more substituents selected from the group consisting of (C$_1$-C$_{10}$)-alkyl, (C$_1$-C$_{10}$)-alkenyl, alkoxy, halo, amine, and hydroxy; and wherein R$_8$ is selected from the group consisting of alkyl, alkenyl, and NR$_9$R$_{10}$, wherein R$_9$ and R$_{10}$ are independently selected from the group consisting of hydrogen, alkyl, and cycloalkyl; and wherein m and n are integers each having a value independently selected from 0 to 10. In some embodiments, a compound of Formula I and/or salt thereof is:

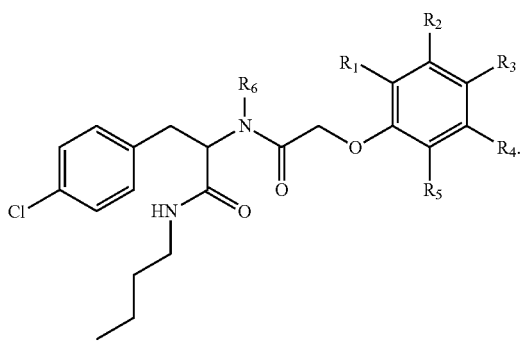

In another aspect, a sirtuin modulating compound and/or salt thereof is of Formula II:

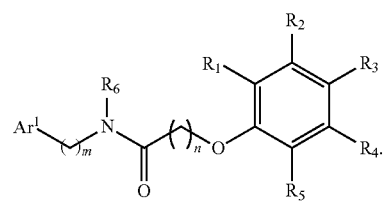

wherein Ar$^1$ is aryl or heteroaryl, R$_1$-R$_6$ are independently selected from the group consisting of hydrogen, alkyl, alkenyl, heteroalkyl, cycloalkyl, heterocycloalkyl, —C(O)R$_7$, alkoxy, halo, nitryl (—NO$_2$), and hydroxy, wherein the Ar$^1$, alkyl, alkenyl, heteroalkyl, cycloalkyl, heterocycloalkyl, aryl, heteroaryl are optionally substituted with one or more substituents selected from the group consisting of (C$_1$-C$_{10}$)-alkyl, (C$_1$-C$_{10}$)-alkenyl, alkoxy, halo, amine, -alkoxy-amide, and hydroxy; and wherein R$_7$ is selected from the group consisting of alkyl, alkenyl, and $NR_8R_9$, wherein $R_8$ and $R_9$ are independently selected from the group consisting of hydrogen, alkyl, and cycloalkyl; and wherein m and n are integers each having a value independently selected from 0 to 10. In some embodiments, for example, a compound of Formula II and/or salt thereof is:

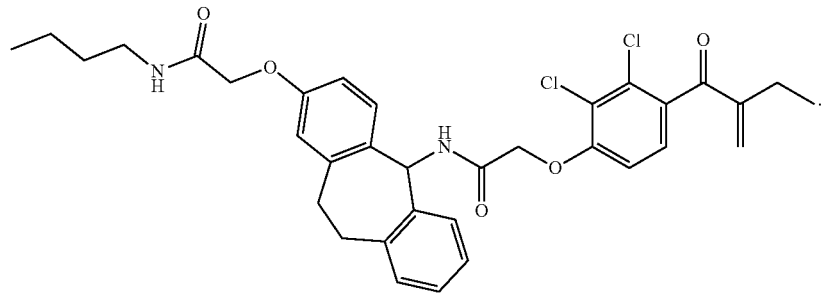 [SMILES: C=C(CC)C(=O)c1ccc(OCC(=O)NC2c3ccccc3CCc3cc(OCC(=O)NCCCC)ccc32)c(Cl)c1Cl]

In another embodiment, a compound of Formula II and/or salt thereof is:

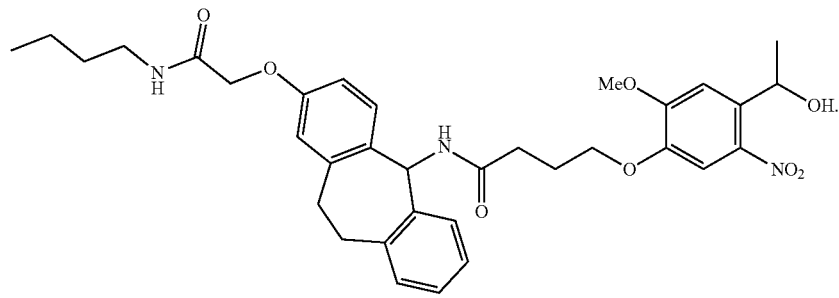 [SMILES: CCCCNC(=O)COc1ccc2c(c1)CCc1ccccc1C2NC(=O)CCCOc1cc([N+](=O)[O-])c(C(C)O)cc1OC]

As described further herein, compounds of Formulas I-V and/or salts thereof, in some embodiments, can modulate SIRT3. These and other embodiments are further described in the following detailed description.

DETAILED DESCRIPTION

Figure 1:
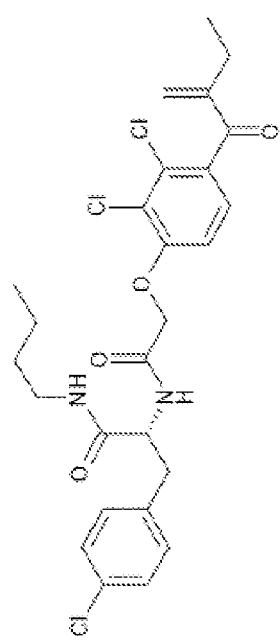
FIGS. 1-27 illustrate compounds of Formula I, according to some embodiments.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$ or $C_1$-$C_{18}$.

The term "alkenyl" as used herein, alone or in combination, refers to a straight or branched chain hydrocarbon group having at least one carbon-carbon double bond and optionally substituted with one or more substituents The term "aryl" as used herein, alone or in combination, refers to an aromatic monocyclic or multicyclic ring system optionally substituted with one or more ring substituents. The term "aryl" includes fused ring systems and non-fused ring systems, where non-fused ring systems include alkylene and sulfonamide linking moieties between the rings.

The term "heteroaryl" as used herein, alone or in combination, refers to an aromatic monocyclic or multicyclic ring system in which one or more of the ring atoms is an element other than carbon, such as nitrogen, oxygen and/or sulfur. The term "heteroaryl" includes fused ring systems and non-fused ring systems, where non-fused ring systems include alkylene and sulfonamide linking moieties between the rings.

The term "cycloalkyl" as used herein, alone or in combination, refers to a non-aromatic, mono- or multicyclic ring system optionally substituted with one or more ring substituents.

The term "heterocycloalkyl" as used herein, alone or in combination, refers to a non-aromatic, mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heteroalkyl" as used herein, alone or in combination, refers to an alkyl moiety as defined above, having one or more carbon atoms in the chain, for example one, two or three carbon atoms, replaced with one or more heteroatoms, which may be the same or different, where the point of attachment to the remainder of the molecule is through a carbon atom of the heteroalkyl radical.

The term "alkoxy" as used herein, alone or in combination, refers to the moiety RO—, where R is alkyl or alkenyl defined above.

The term "halo" as used herein, alone or in combination, refers to elements of Group VIIA of the Periodic Table (halogens). Depending on chemical environment, halo can be in a neutral or anionic state.

Compounds of Formulas I and II were included in a Sirt3 docking study as follows.

Compounds of Formulas I and II exhibiting modulation of Sirt3 are labeled reference compounds.

Modulating activity of reference compounds are further illustrated below. Additional compounds of Formula I and II have been developed/derived to exhibit one or more structural similarities with the reference compounds. Initial 3D structures of the compounds were generated from SMILES strings using RDKit (2019 version), or, if this failed, Openbabel version 3.0. In cases of ambiguity (axial vs equatorial substitution for example), all conformers were generated. In addition, all stereoisomers were generated for racemates. For structures with non-standard ring puckers, structures were minimised using DFT to ensure feasible geometries were used for docking. This was carried out using ORCA version 3.0.1. GOLD v 5.2 was used to dock all compounds into Sirt3 using 3 PDB files, 4BVG and 4FVT, along with an internally-generated xray structure of human Sirt3 (called Xtal). In each case the binding pocket was restricted to anything within 20A of the ligand in the original PDB file, and 30 docks were requested for each ligand. All other options were set to the default options. An in-house algorithm was used to identify and assess the quality of all hydrogen bonds (H-bonds) made between ligand and protein and this information was used along with the GOLD docking score to select optimal solutions. Two docks were selected for each compound, namely the highest-scoring dock that contained the most H-bonds, and the highest scoring of the remaining docks. These docks were manually assessed and compared with the parent reference compound used to seed the design.

In the following tables of docking results, the highest-scoring dock independently of the number of hydrogen bonds was chosen. Compounds with a docking score at least higher than 90% of the docking score (GoldScore) of the reference compound have been considered as a potential Sirt3 modulator. Compounds of Formulas I and II identified in the docking study as potential Sirt3 modulators are provided in FIGS. 1-57 and Tables 1-6 below.

TABLE 1

Compounds of Formula I Sirt3 Docking Results
4 FVT Model

Figure 2:
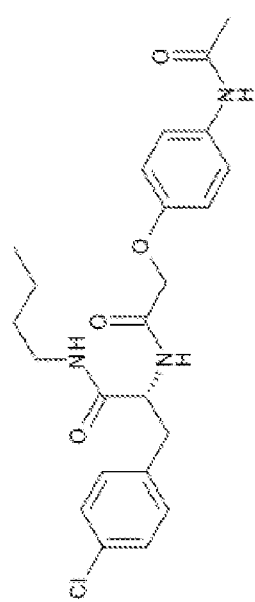
Figure 4:
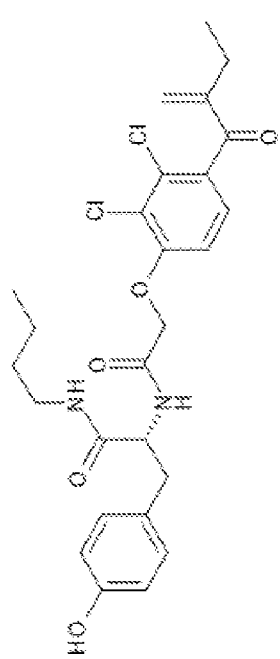
Figure 5:
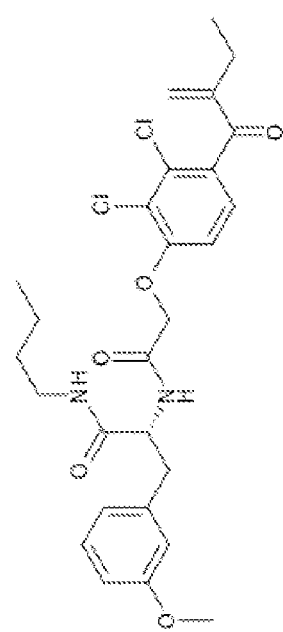
Figure 6:
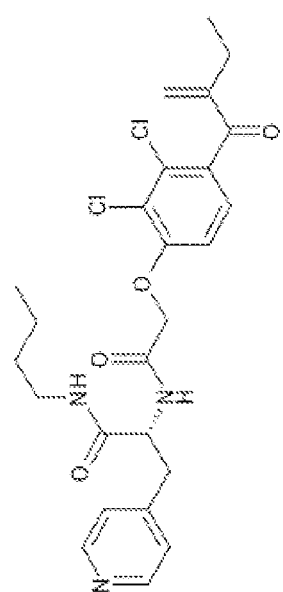

| Compound | Nb of H-Bond | Best Docking Score |
|---|---|---|
| FIG. 1 (Reference) | 2 | 71.96 |
| FIG. 2 | 1 | 69.10 |
| FIG. 4 | 2 | 70.26 |
| FIG. 5 | 0 | 72.34 |
| FIG. 6 | 0 | 72.83 |

TABLE 1-continued

Compounds of Formula I Sirt3 Docking Results
4 FVT Model

Figure 7:
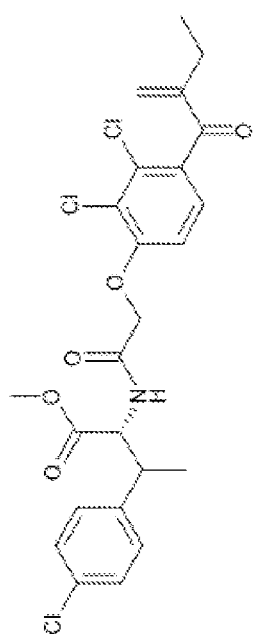
Figure 8:
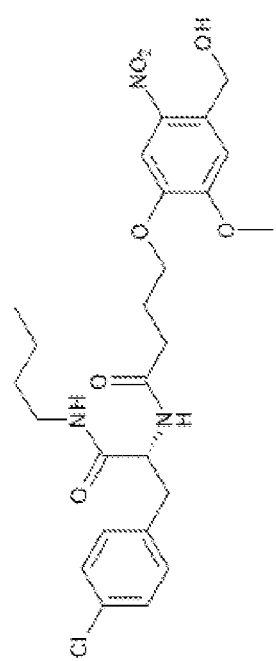
Figure 9:
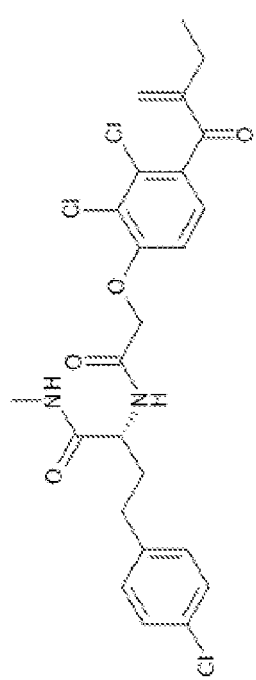
Figure 10:
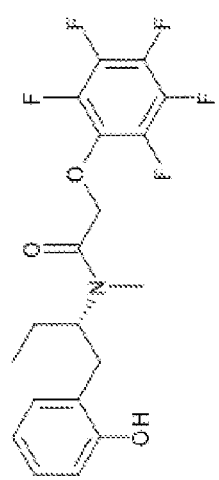
Figure 11:
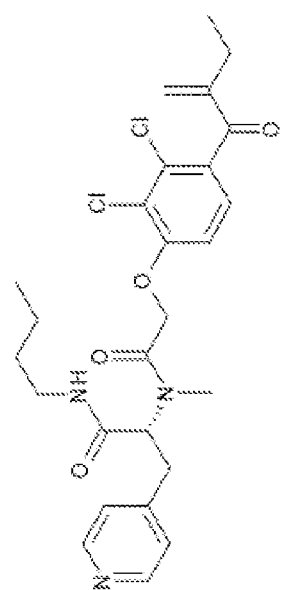
Figure 12:
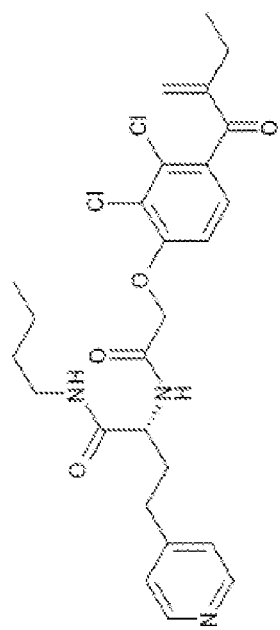
Figure 13:
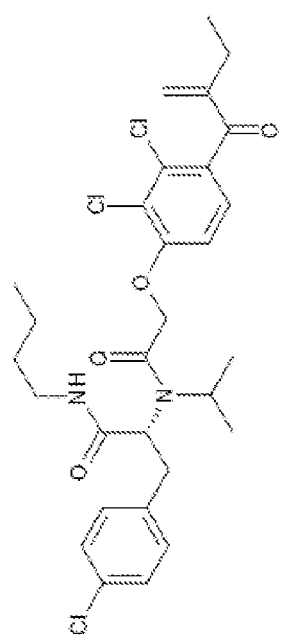
Figure 14:
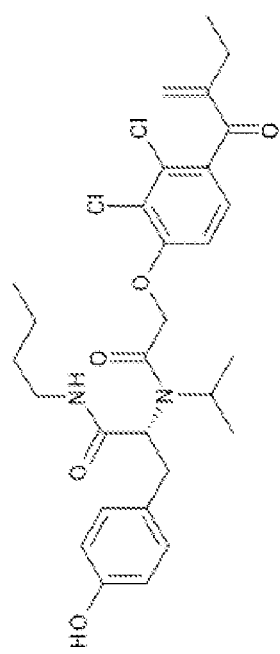
Figure 15:
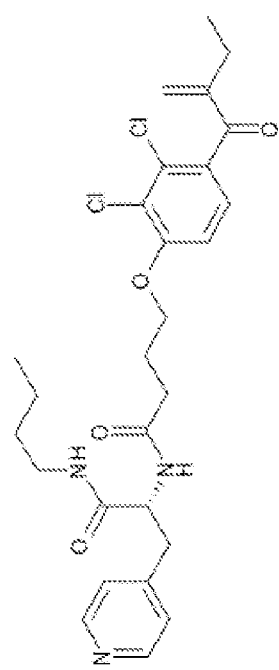
Figure 16:
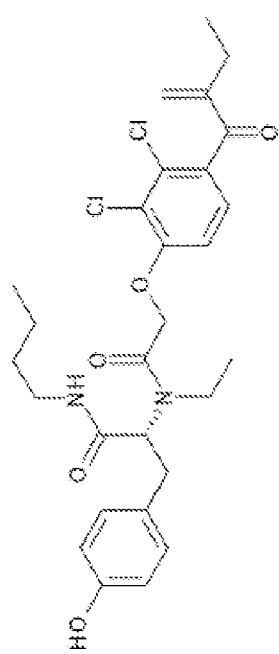
Figure 17:
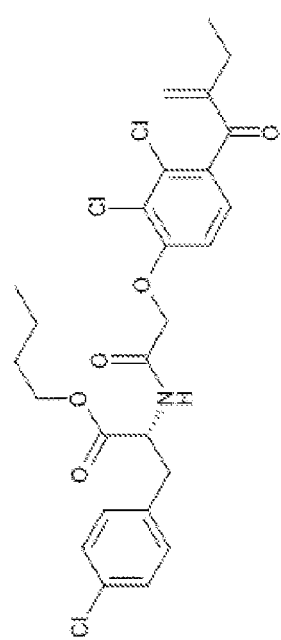
Figure 18:
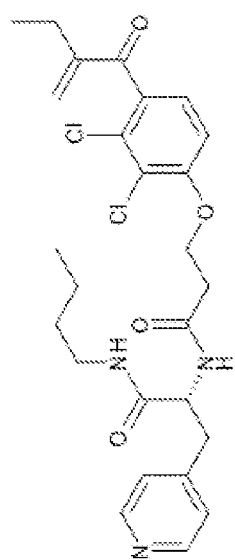
Figure 19:
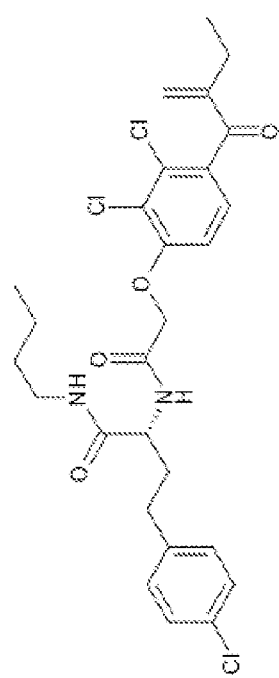
Figure 20:
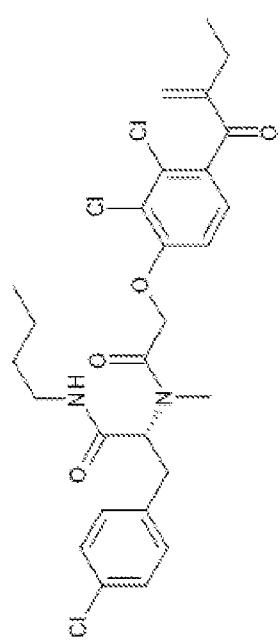
Figure 21:
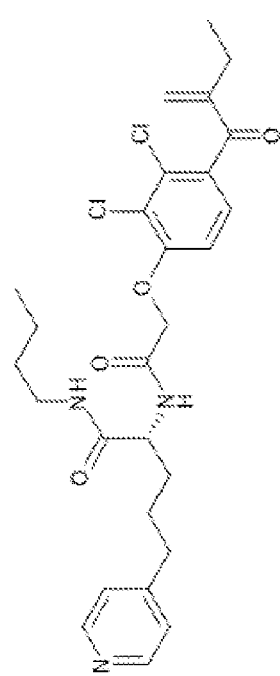
Figure 22:
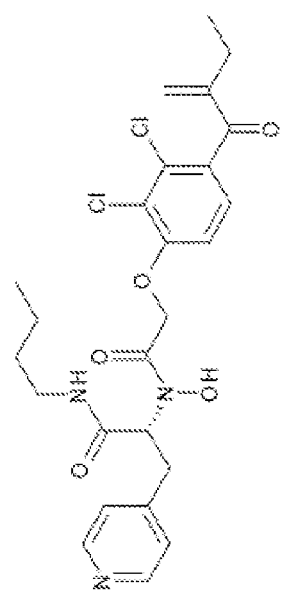
Figure 23:
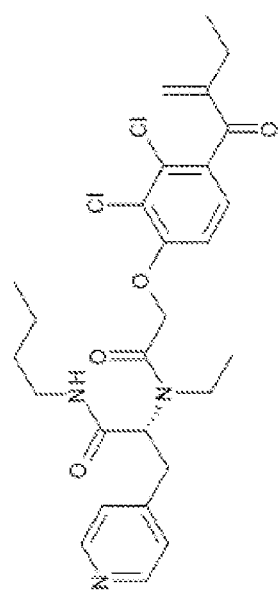
Figure 24:
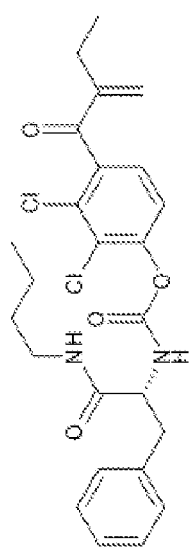
Figure 25:
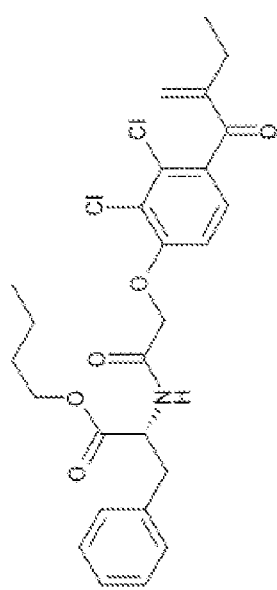
Figure 26:
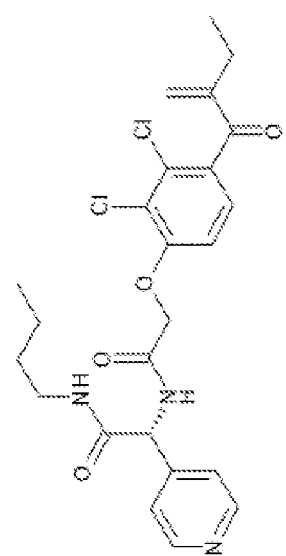
Figure 27:
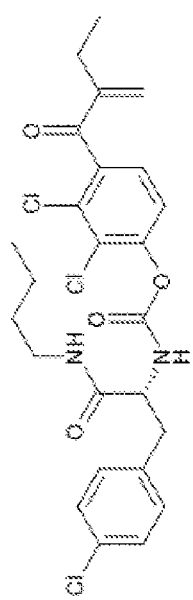

| Compound | Nb of H-Bond | Best Docking Score |
|---|---|---|
| FIG. 7 | 0 | 66.10 |
| FIG. 8 | 0 | 73.20 |
| FIG. 9 | 0 | 70.20 |
| FIG. 10 | 1 | 67.60 |
| FIG. 11 | 2 | 83.07 |
| FIG. 12 | 0 | 90.11 |
| FIG. 13 | 0 | 87.45 |
| FIG. 14 | 1 | 82.05 |
| FIG. 15 | 0 | 97.28 |
| FIG. 16 | 3 | 80.92 |
| FIG. 17 | 0 | 88.97 |
| FIG. 18 | 2 | 92.46 |
| FIG. 19 | 2 | 96.87 |
| FIG. 20 | 0 | 82.58 |
| FIG. 21 | 0 | 97.27 |
| FIG. 22 | 0 | 82.78 |
| FIG. 23 | 0 | 81.50 |
| FIG. 24 | 0 | 81.26 |
| FIG. 25 | 0 | 84.89 |
| FIG. 26 | 0 | 83.61 |
| FIG. 27 | 1 | 77.59 |

TABLE 2

Compounds of Formula I Sirt3 Docking Results
4 BVG Model

| Compound | Nb of H-Bond | Best Docking Score |
|---|---|---|
| FIG. 1 (Reference) | 0 | 86.53 |
| FIG. 4 | 1 | 93.00 |
| FIG. 5 | 0 | 80.76 |
| FIG. 6 | 1 | 90.46 |
| FIG. 8 | 1 | 80.61 |
| FIG. 9 | 1 | 83.91 |

TABLE 3

Compounds of Formula I Sirt3 Docking Results
Xtal Model

Figure 3:
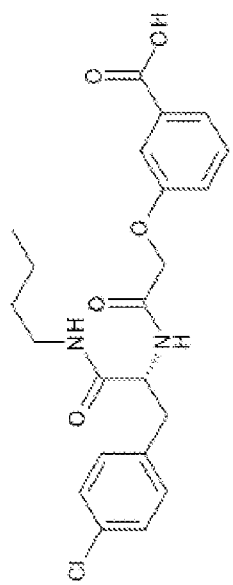

| Compound | Nb of H-Bond | Best Docking Score |
|---|---|---|
| FIG. 1 (Reference) | 0 | 88.31 |
| FIG. 3 | 0 | 80.70 |
| FIG. 4 | 0 | 80.82 |
| FIG. 6 | 1 | 79.80 |
| FIG. 8 | 0 | 88.13 |
| FIG. 9 | 1 | 83.67 |
| FIG. 10 | 1 | 84.41 |
| FIG. 11 | 0 | 92.38 |
| FIG. 12 | 1 | 82.98 |
| FIG. 13 | 0 | 79.84 |
| FIG. 14 | 0 | 80.38 |
| FIG. 15 | 0 | 92.72 |
| FIG. 16 | 1 | 79.80 |
| FIG. 17 | 1 | 82.55 |
| FIG. 18 | 1 | 87.22 |
| FIG. 19 | 0 | 91.49 |
| FIG. 20 | 0 | 82.49 |
| FIG. 21 | 1 | 83.21 |

TABLE 4

Compounds of Formula II Sirt3 Docking Results
4 FVT Model

Figure 28:
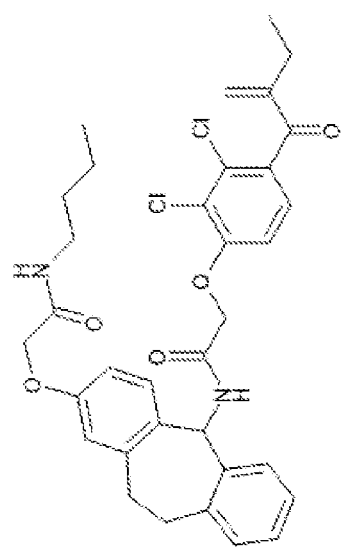
FIGS. 28-57 illustrate compounds of Formula II, according to some embodiments.
Figure 29:
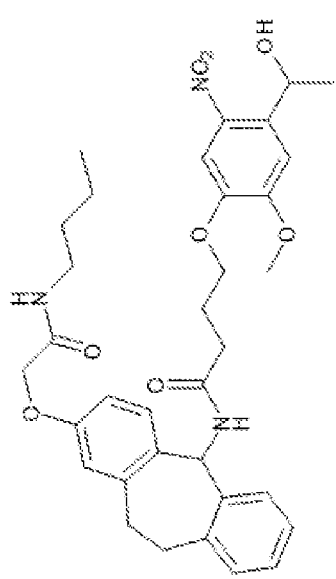
Figure 30:
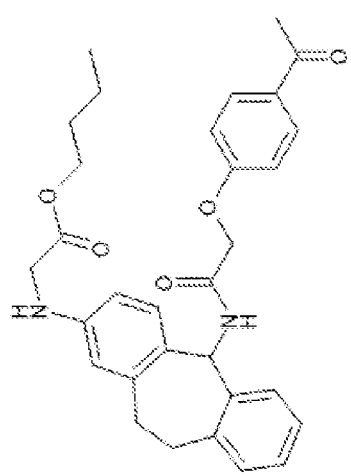
Figure 31:
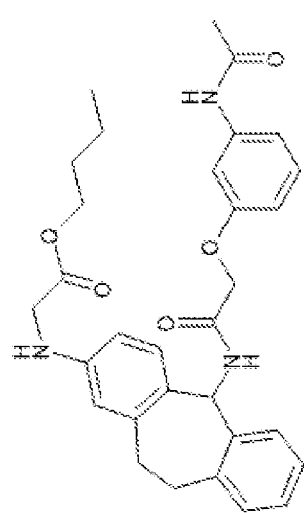
Figure 32:
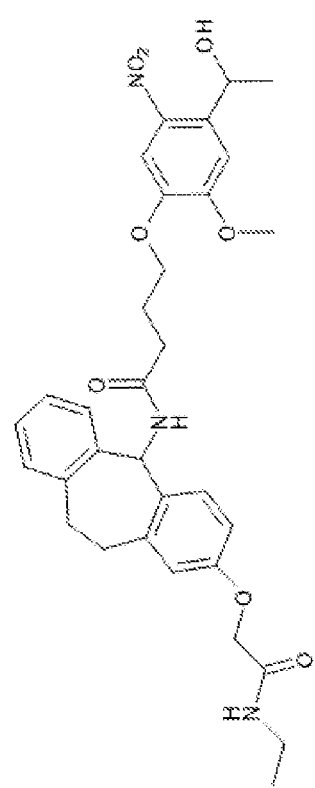
Figure 33:
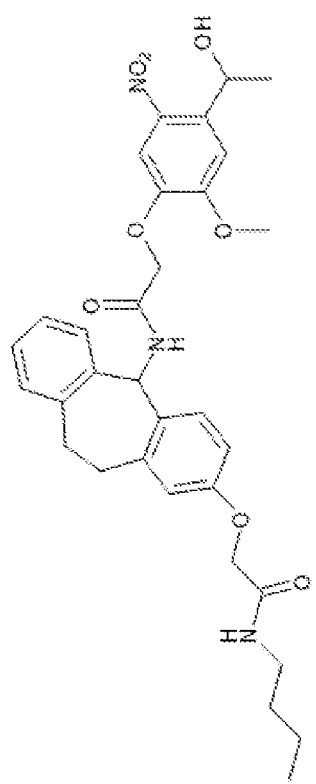
Figure 34:
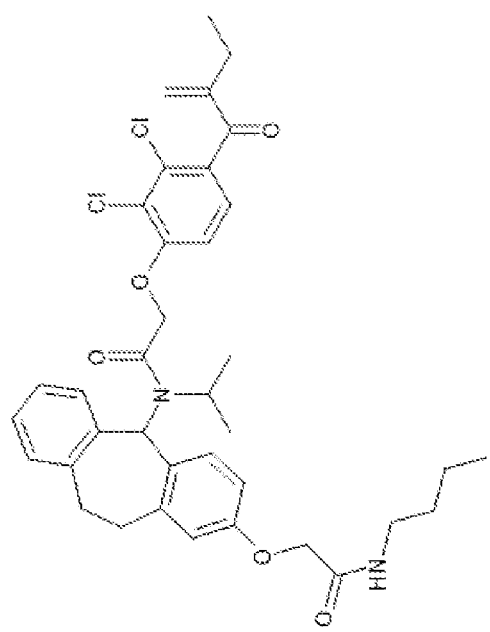
Figure 35:
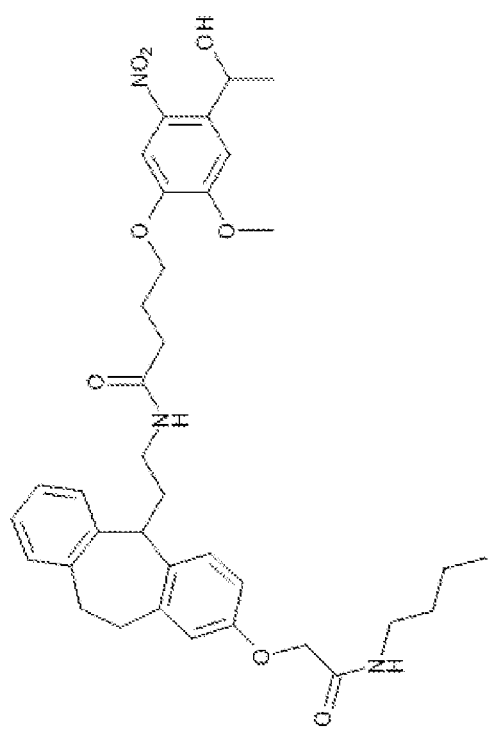
Figure 36:
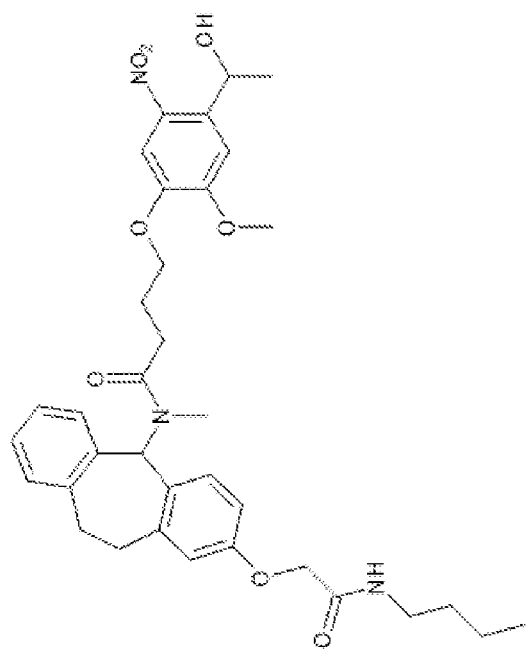
Figure 37:
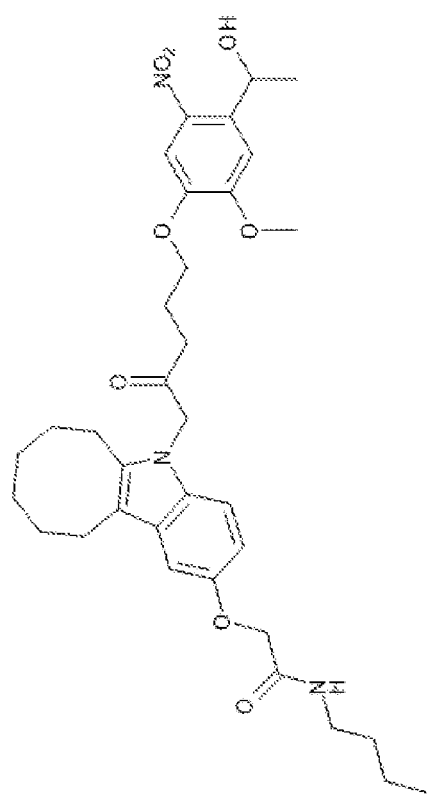
Figure 38:
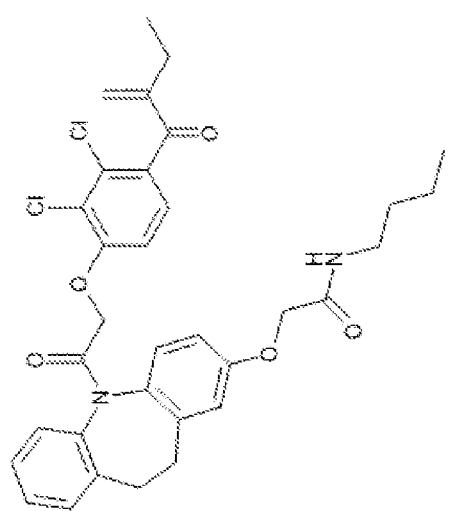
Figure 39:
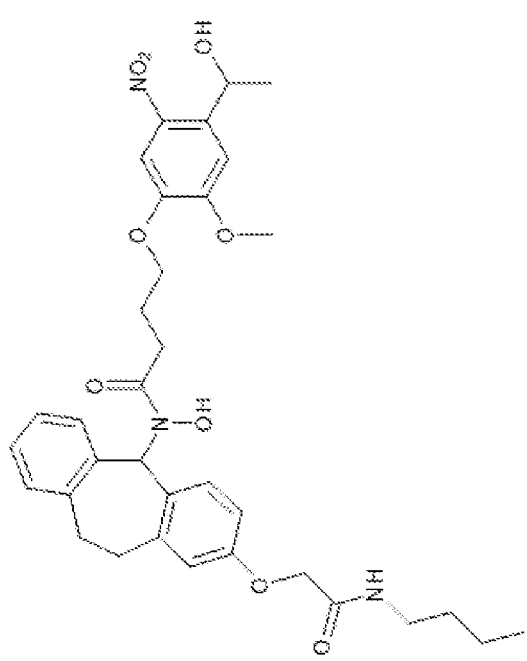
Figure 40:
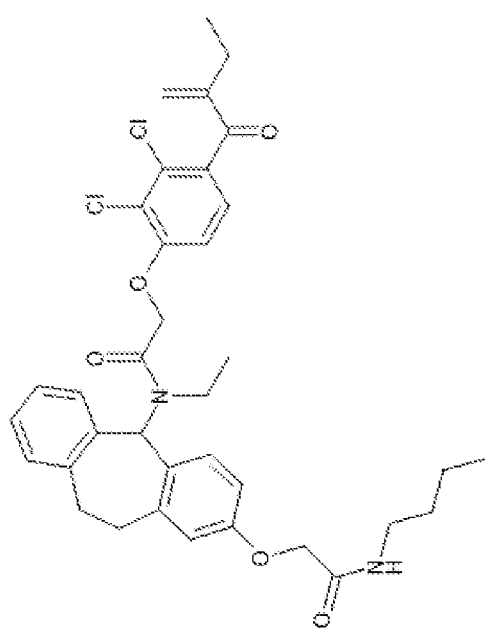
Figure 41:
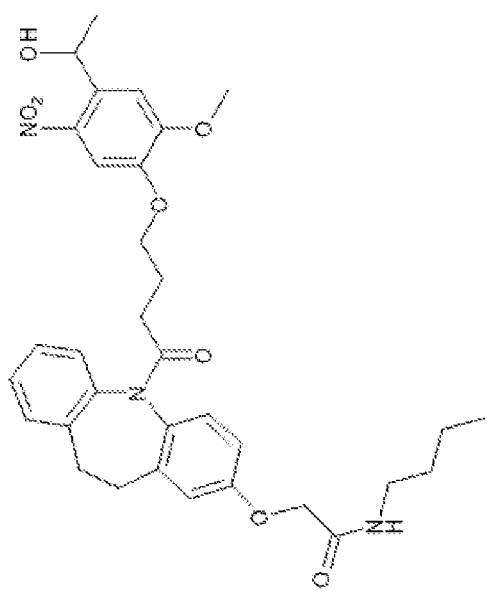
Figure 42:
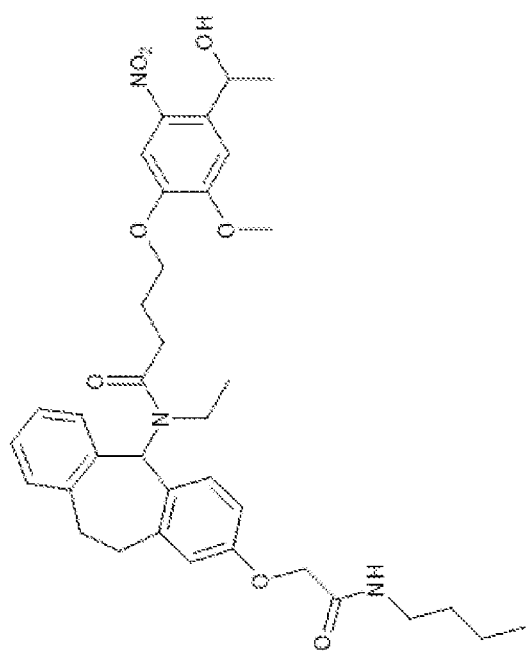
Figure 43:
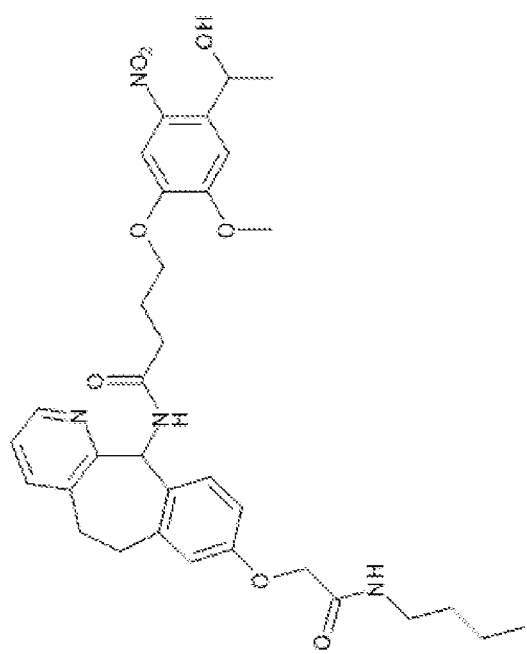
Figure 44:
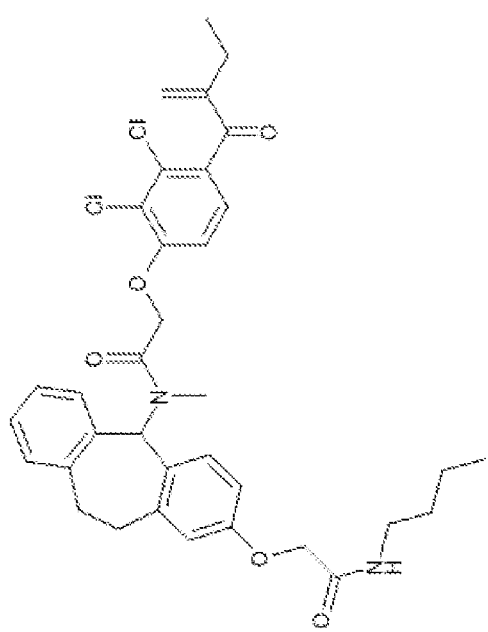
Figure 45:
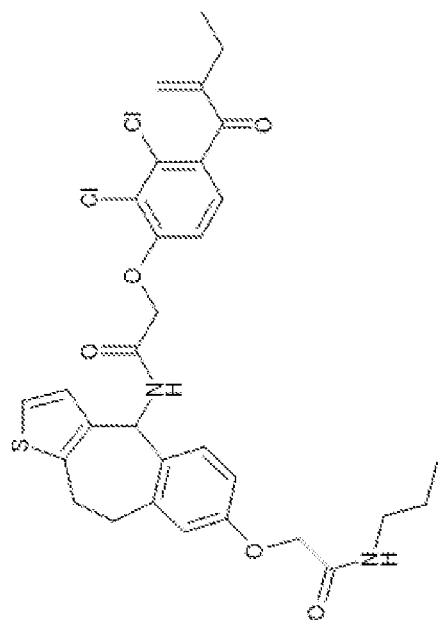
Figure 46:
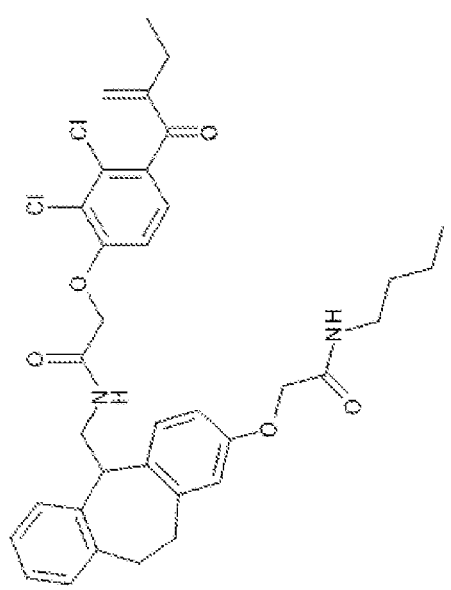
Figure 47:
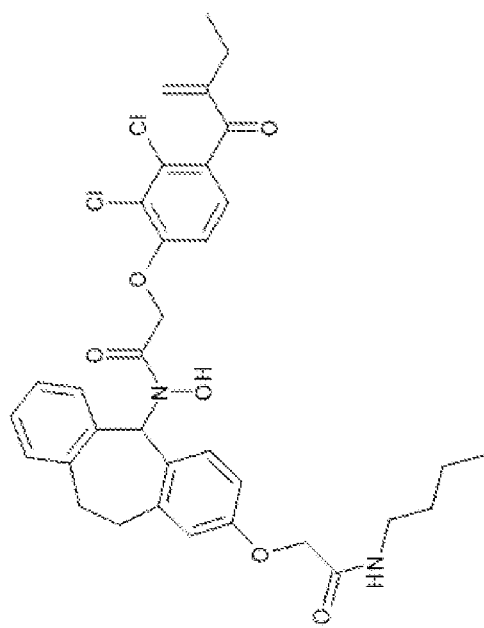
Figure 48:
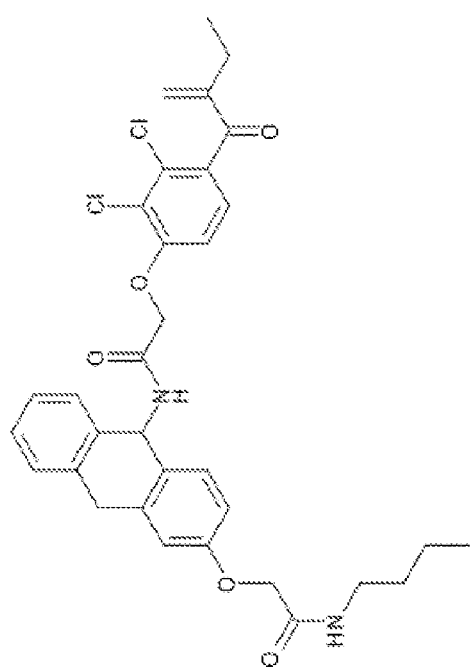
Figure 49:
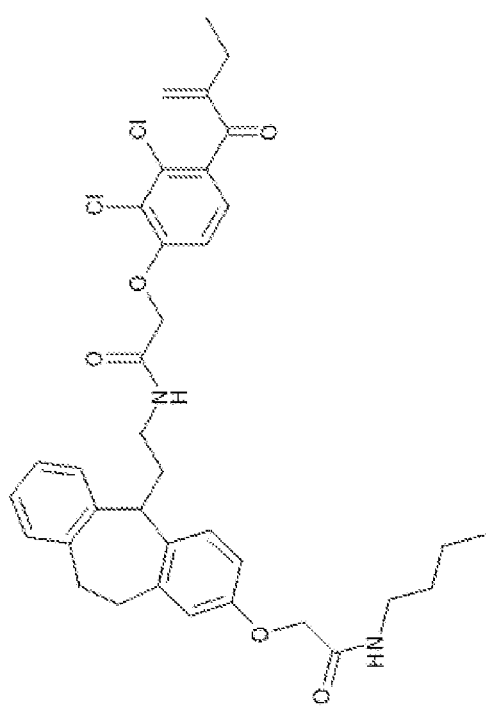
Figure 50:
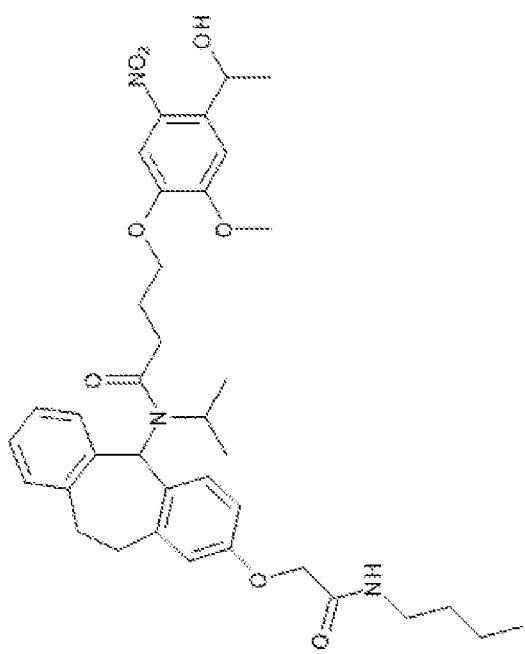
Figure 51:
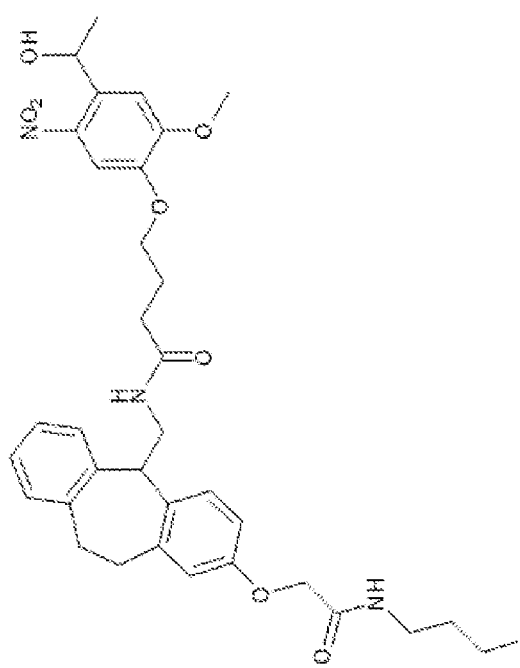
Figure 52:
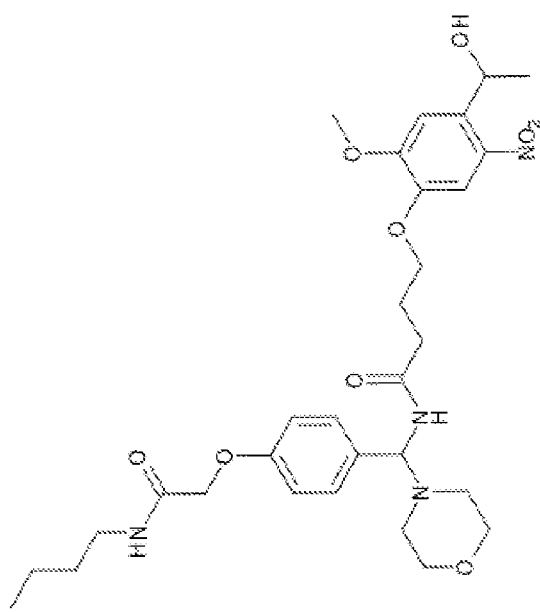
Figure 53:
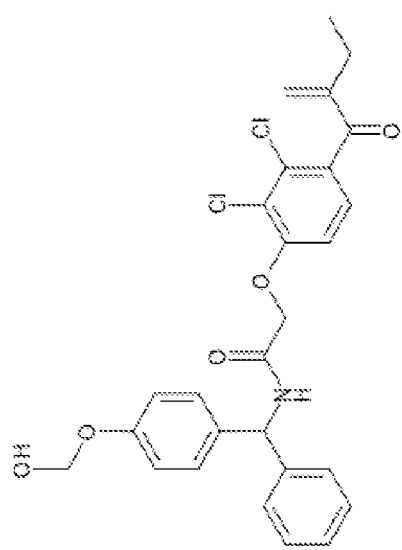
Figure 54:
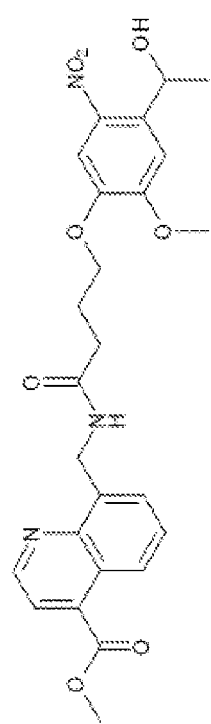
Figure 55:
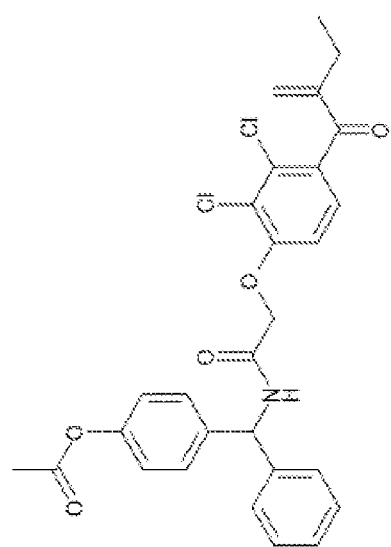
Figure 56:
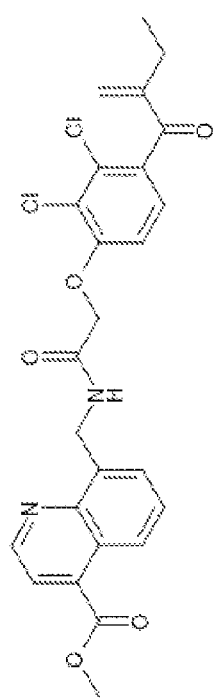

| Compound | Nb of H-Bond | Best Docking Score |
|---|---|---|
| FIG. 28 (Reference) | 1 | 91.31 |
| FIG. 29 (Reference) | 0 | 90.97 |
| FIG. 30 | 1 | 83.72 |
| FIG. 31 | 0 | 85.07 |
| FIG. 32 | 0 | 86.29 |
| FIG. 33 | 3 | 87.46 |
| FIG. 34 | 1 | 92.51 |
| FIG. 35 | 2 | 102.10 |
| FIG. 36 | 4 | 95.75 |
| FIG. 37 | 3 | 96.86 |
| FIG. 38 | 1 | 87.81 |
| FIG. 39 | 2 | 97.69 |
| FIG. 40 | 0 | 100.17 |
| FIG. 41 | 0 | 90.66 |
| FIG. 42 | 1 | 99.19 |
| FIG. 43 | 0 | 89.02 |
| FIG. 44 | 1 | 93.30 |
| FIG. 45 | 1 | 94.52 |
| FIG. 46 | 1 | 108.81 |
| FIG. 47 | 1 | 94.38 |
| FIG. 48 | 1 | 102.30 |
| FIG. 49 | 3 | 108.96 |
| FIG. 50 | 0 | 95.99 |
| FIG. 51 | 1 | 95.93 |
| FIG. 52 | 0 | 90.96 |
| FIG. 53 | 1 | 94.41 |
| FIG. 54 | 2 | 81.91 |
| FIG. 55 | 0 | 88.00 |
| FIG. 56 | 2 | 90.43 |

TABLE 5

Compounds of Formula II Sirt3 Docking Results
4 BVG Model

| Compound | Nb of H-Bond | Best Docking Score |
|---|---|---|
| FIG. 28 (Reference) | 2 | 95.77 |
| FIG. 29 (Reference) | 1 | 98.38 |
| FIG. 32 | 2 | 93.23 |
| FIG. 33 | 4 | 88.79 |
| FIG. 34 | 0 | 92.49 |
| FIG. 35 | 3 | 105.75 |
| FIG. 36 | 2 | 92.53 |
| FIG. 37 | 0 | 96.85 |
| FIG. 38 | 0 | 87.47 |
| FIG. 39 | 0 | 99.79 |
| FIG. 40 | 1 | 91.56 |
| FIG. 41 | 1 | 95.53 |
| FIG. 42 | 0 | 94.69 |
| FIG. 43 | 3 | 94.38 |
| FIG. 44 | 0 | 89.59 |
| FIG. 45 | 0 | 87.03 |
| FIG. 46 | 0 | 95.61 |
| FIG. 47 | 2 | 92.86 |
| FIG. 48 | 0 | 90.21 |
| FIG. 49 | 1 | 102.22 |
| FIG. 50 | 1 | 94.30 |
| FIG. 51 | 0 | 99.92 |

TABLE 6

Compounds of Formula II Sirt3 Docking Results
Xtal Model

Figure 57:
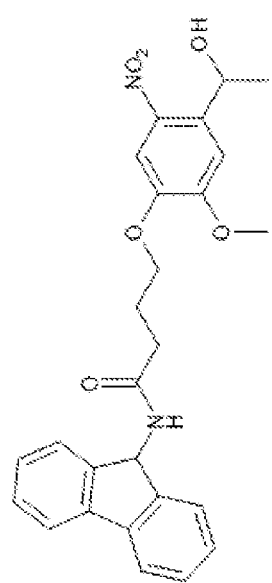

| Compound | Nb of H-Bond | Best Docking Score |
|---|---|---|
| FIG. 28 (Reference) | 2 | 107.53 |
| FIG. 29 (Reference) | 1 | 96.91 |
| FIG. 30 | 1 | 95.99 |
| FIG. 31 | 1 | 96.72 |
| FIG. 32 | 0 | 95.44 |
| FIG. 33 | 1 | 94.97 |
| FIG. 34 | 0 | 89.99 |
| FIG. 35 | 0 | 117.32 |
| FIG. 36 | 1 | 98.32 |
| FIG. 37 | 0 | 106.95 |
| FIG. 38 | 1 | 92.88 |
| FIG. 39 | 2 | 105.79 |
| FIG. 40 | 1 | 94.38 |
| FIG. 41 | 2 | 98.79 |
| FIG. 42 | 1 | 102.36 |
| FIG. 43 | 2 | 97.40 |
| FIG. 44 | 0 | 92.04 |
| FIG. 45 | 1 | 96.95 |
| FIG. 46 | 1 | 103.54 |
| FIG. 47 | 2 | 93.67 |
| FIG. 48 | 2 | 98.20 |
| FIG. 49 | 1 | 110.01 |
| FIG. 50 | 1 | 97.73 |
| FIG. 51 | 0 | 111.44 |
| FIG. 52 | 2 | 93.62 |
| FIG. 57 | 1 | 94.59 |

Sirt3 Modulation Effect Under Steady-State Conditions

Figure 58:
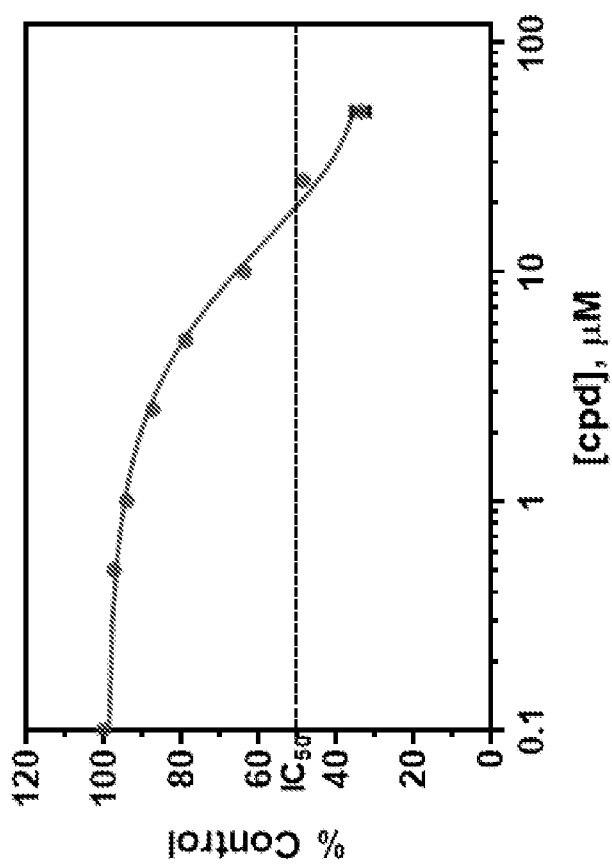
FIG. 58 illustrates a dose-response curve of the compound of FIG. 29 under steady state condition where $[NAD^+]=1$ mM, [FdL2 peptide]=50 µM, $[E_0]/[NAD^+]=0.0015$ at 30 min time point (N=3). The line at 50% corresponds to a conservative estimate for IC50 because the compounds do not produce 100% inhibition upon saturation.

Reference compounds of FIGS. 1 and 28-29 were screened using a fast fluorescence-base assay (FdL) under the steady state condition (low enzyme concentration, high reaction time) to validate binding and activity modulation, and show different degrees of inhibitory effect. As set forth in Table 7, it was found that the Sirt3 deacylation activity was inhibited by 66.3% in the presence of 50 μM of reference compound of FIG. 29. FIG. 58 illustrates a dose-response curve of the compound of FIG. 29 under steady state condition where $[NAD^+]=1$ mM, [FdL2 peptide]=50 μM, $[E_0]/[NAD^+]=0.0015$ at 30 min time point (N=3). The line at 50% corresponds to a conservative estimate for IC50 because the compounds do not produce 100% inhibition upon saturation.

TABLE 7

Potency of compounds on Sirt3 deacylation activity
under steady state conditions

| | % Control | | |
|---|---|---|---|
| Compound | 50 μM or maximum | 10 μM | 1 μM |
| FIG. 29 | 33.7 ± 2.4 | 63.7 ± 0.6 | 94.1 ± 1.2 |
| FIG. 28 | 68.7 ± 4.0 | 75.5 ± 2.3 | 80.4 ± 3.1 |
| FIG. 1 | 73.6 ± 2.4 | 82.8 ± 2.3 | 95.7 ± 2.6 |

It was also found that the inhibition level increases as the dose increases. Overall, the EC50 values of compounds of Formulas I and II herein are expected to fall in the 10-20 μM range, if not lower concentrations.

Non-Steady State Activation of Sirt3

As an established Sirt3 activator, HKL was studied to investigate how the time series of activity modulation depends on the concentration $[E]_0$ of enzyme. The activation of Sirt3 was tested and confirmed by HPLC-assay under non-steady state condition (high enzyme concentration, short reaction time) in the presence of two out of reference compounds of FIGS. 1 and 29. The results are provided in Table 8. This non-steady state was studied using 50 U or 100 U of enzyme and 50 μM of $NAD^+$, $E_0/NAD^+=0.3-0.6$ and 2 minute time point to limit the substrate concentration such that steady state is achieved later. The NAD⁺ concentration used in our non-steady state study is close to physiological concentration during aging since mitochondrial NAD⁺ is ~200 μM in young age and can drop by 50% or more in old age.

TABLE 8

Potency of compounds on Sirt3 deacylation activity under non-steady state conditions

| Compound | % Control (10 μM) | $[E]_0/[NAD^+]_0$ |
|---|---|---|
| FIG. 1 | 103.5 ± 3.3 | 0.3 |
|  | 106.8 ± 1.6 | 0.6 |
| FIG. 29 | 106.8 ± 2.0 | 0.3 |
|  | 121.5 ± 1.6 | 0.6 |

Materials and Method

Activity Assays of Hit Compounds

Chemicals and Reagents

MnSOD (KGELLEAI-(KAc)-RDFGSFDKF) was synthesized by GenScript (Piscataway, NJ). FdL2 (QPKK$^{AC}$-AMC) peptide, also called p53-AMC peptide, was purchased from Enzo Life Sciences (Farmingdale, NY). Carba-NAD was synthesized by Dalton Pharma (Toronto, ON). The hSirt3$^{118-399}$ was purchased from Xtal Biostructures (Natick, MA). Virtual screening hits were supplied from ChemBridge Corp. (San Diego, CA).

Effect of Hit Compounds on hSirt3$^{118-399}$ Deacetylation Activity

HPLC Assay Using Native Peptide

Enzymatic reactions included either 1 mM NAD⁺ and 50 μM MnSOD peptide or 50 μM NAD⁺ and 600 μM peptide substrate in presence of hit compounds (10 μM), in a buffer (50 mM TRIS-HCl, 137 mM NaCl, 2.7 mM KCl, and 1 mM MgCl₂, pH 8.0 and 5% DMSO). The reaction was initiated by adding 5U hSirt3$^{118-399}$ and incubated at 37° C. for 30 minutes. The reaction was terminated by 2% TFA. The peptide product and substrate were resolved using HPLC. Solvent A was composed of 90% HPLC grade water and 10% acetonitrile with 0.02% (v/v) TFA. Solvent B was composed of acetonitrile with 0.05% (v/v) TFA. A linear gradient was performed for 20 min from 0% B to 51% (v/v) B. Solvent B percentage was increased to 100% within 5 minutes. Then returned to the starting conditions (0% B) within 5 min. Solvent A percentage (100%) was maintained at 100% for 5 additional minutes (36 min total run time).

Syntheses of Reference Compounds of FIG. 1, FIG. 28, FIG. 29

FIG. 1

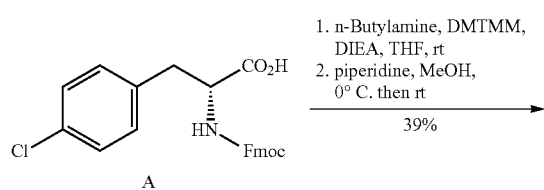

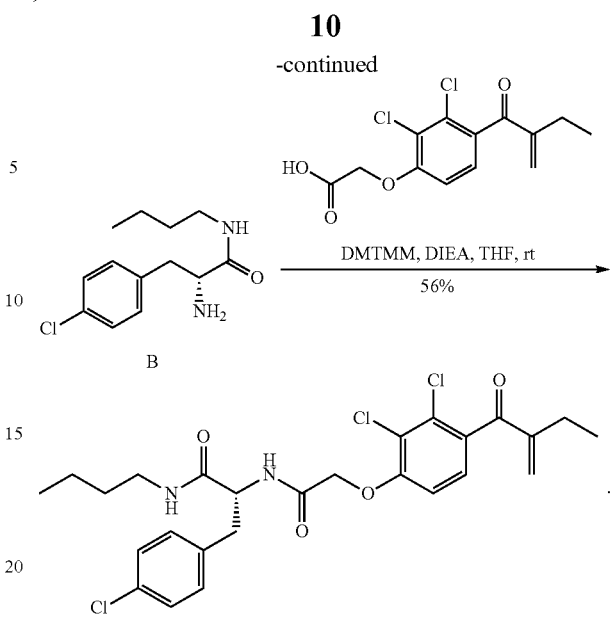

FIG 1

Synthesis of (2R)-2-amino-N-butyl-3-(4-chlorophenyl) propanamide) (B)

To a solution of Fmoc-4-chloro-D-phenylalanine (A) (4.90 g, 11.7 mmol) in THF (45 mL), was added DMT·MM (3.88 g, 14.0 mmol) and DIEA (4.07 mL, 23.4 mmol). After stirring at RT for 15 min, n-butylamine was added (0.94 g, 12.9 mmol). The reaction mixture was stirred at RT overnight. The mixture was concentrated under reduced pressure then 150 mL of water was added. A precipitate was formed, it was filtered and washed with water (250 mL×2). The white solid was dried in vacuum oven at 40° C. overnight and then directly engaged into the next step.

To a solution of the obtained white powder in methanol (100 mL) at 0° C., was added piperidine (15.60 mL, 157.8 mmol). The mixture was slowly allowed to warm at RT and stirred at RT overnight.

The mixture was concentrated under reduced pressure. The crude product was roughly purified by flash column chromatography (DCM/MeOH gradient) to afford (2R)-2-amino-N-butyl-3-(4-chlorophenyl)propanamide) (B) (1.35 g, 39% yield) as a yellow solid. The compound purity was not good enough to provide a reliable NMR description, but the product was used in the downstream chemistry without further purification.

LCMS Calculated for $C_{13}H_{19}ClN_2O$, 254.1, Observed [M+H]⁺ 255.2

Synthesis of (2R)—N-butyl-3-(4-chlorophenyl)-2-[[2-[2, 3-dichloro-4-(2-methylenebutanoyl)phenoxy]acetyl]amino] propanamide (FIG. 1)

To a solution of Ethacrynic acid (257.7 mg, 0.85 mmol) in 3 mL of THF at RT, were added DMT·MM (235.2 mg, 0.85 mmol) then DIEA (245 μL, 1.41 mmol) successively. The reactions were stirred at RT for 30 min then 2 mL of a solution of (2R)-2-amino-N-butyl-3-(4-chlorophenyl)propanamide) (B) (180 mg in 2 mL of THF) was added to each reaction. The reactions were stirred at RT overnight. A precipitate was formed. The insoluble was filtered and rinsed with THF (10 mL×2). the filtrate was concentrated under vacuum to give colored powders. Products were purified by flash column chromatography (DCM/MeOH gradient) to give: (2R)—N-butyl-3-(4-chlorophenyl)-2-[[2-[2,3-dichloro-4-(2-methylenebutanoyl)phenoxy]acetyl]amino]propanamide (FIG. 1) (70 mg, 18% yield) as a white solid.

LCMS Calculated for C26H29Cl3N2O4, 538.1, Observed [M+H]+ 539.1

1H NMR (80 MHz, DMSO-d6) δ 8.48-7.87 (m, 2H), 7.49-7.10 (m, 5H), 6.81 (d, J=8.7 Hz, 1H), 6.07 (s, 1H), 5.55 (s, 1H), 4.71-4.20 (m, 3H), 3.32-2.81 (m, 4H), 2.29 (d, J=7.4 Hz, 2H), 1.51-0.80 (m, 10H).

13C NMR (20 MHz, DMSO-d6) δ 195.0, 170.0, 166.2, 155.3, 149.4, 136.5, 132.4, 131.1, 129.4, 128.0, 127.3, 121.1, 111.6, 67.5, 53.4, 38.2, 31.1, 23.0, 19.5, 13.6, 12.4

HRMS Calculated for C26H30Cl3N2O4 ([M+H]+) 539.1265, found 539.1268.

FIG. 28 and FIG. 29

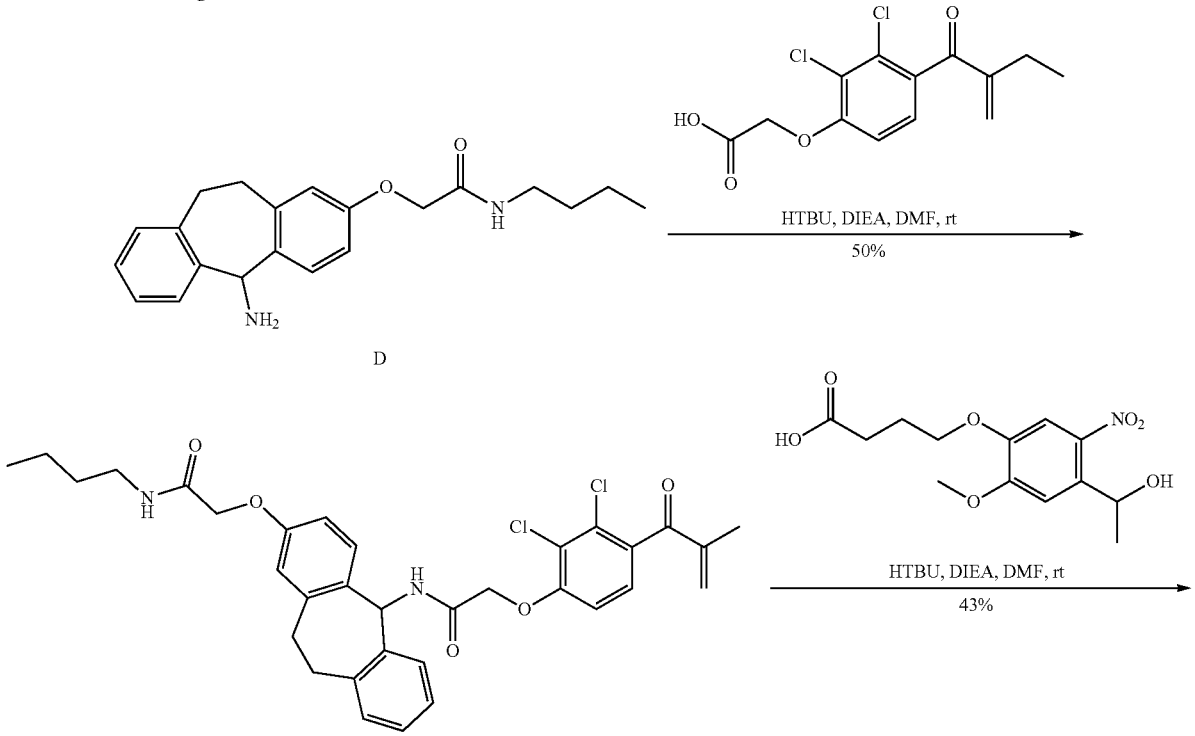

FIG 28

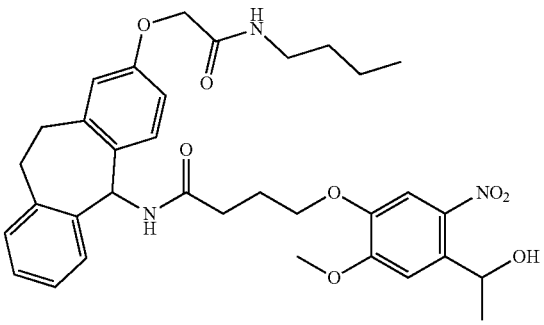

FIG 29

Synthesis of 2-[(2-amino-6-tricyclo[9.4.0.03,8]pentadeca-1(11),3(8),4,6,12,14-hexaenyl)oxy]-N-butyl-acetamide (D)

To a solution of Ramage Linker or Fmoc-Suberol (C) (5.00 g, 9.90 mmol) in DMF (50 mL), was added HBTU (5.60 g, 14.9 mmol) and NaHCO3 (1.66 g, 19.8 mmol). After stirring at RT for 0.5 h, n-butylamine was added (0.86 g, 11.9 mmol). The reaction mixture was stirred at RT for 2 h then quenched by adding 380 mL of water. A precipitate was formed, stirred at RT for 1 h then filtered and washed with water (250 mL×2). The beige solid was dried in vacuum oven overnight and then directly engaged into the next step. To a solution of the obtained beige powder in methanol (100 mL) at 0-5° C., was added piperidine (13.20 mL, 133.7 mmol). The mixture was slowly allowed to warm at RT and stirred at RT for 1 h. THF (200 mL) was added to improve the solubility and the mixture was stirred at RT overnight.

The mixture was concentrated under reduced pressure. The crude product was purified by flash column chromatography (DCM/MeOH gradient) to give 2-[(2-amino-6-tricyclo[9.4.0.03,8]pentadeca-1(11),3(8),4,6,12,14-hexaenyl)oxy]-N-butyl-acetamide (D) (3 g, 85% yield) as a beige solid.

LCMS Calculated for $C_{21}H_{26}N_2O_2$, 338.2, Observed [M+Na]$^+$361.2

1H NMR (80 MHz, DMSO-d6) δ 8.16-7.77 (m, 1H), 7.61-7.24 (m, 2H), 7.21-6.94 (m, 3H), 6.88-6.53 (m, 2H), 5.40 (s, 1H), 4.38 (s, 2H), 3.22-2.89 (m, 6H), 1.52-1.09 (m, 4H), 0.99-0.66 (m, 3H)

13C NMR (100 MHz, DMSO-d6) δ 167.4, 156.6, 142.9, 139.4, 138.2, 135.4, 129.6, 127.3, 126.7, 125.8, 125.7, 116.1, 111.5, 67.0, 55.6, 37.9, 32.0, 31.5, 31.2, 19.5, 13.6

HRMS Calculated for $C_{21}H_{27}N_2O_2$ ([M+H]$^+$) 322.1801, found 322.1807.

Synthesis of N-butyl-2-[[2-[[2-[2,3-dichloro-4-(2-methylprop-2-enoyl)phenoxy]acetyl]amino]-6-tricyclo[9.4.0.03,8]pentadeca-1(11),3(8),4,6,12,14-hexaenyl]oxy]acetamide (FIG. 28)

To a solution of Ethacrynic acid (161 mg, 0.53 mmol) in 2 mL of DMF at RT, were added HBTU (252.3, 0.67 mmol) then DIEA (153.5 μL, 0.89 mmol) successively. The reaction was stirred at RT for 30 min then 2-[(2-amino-6-tricyclo[9.4.0.03,8]pentadeca-1(11),3(8),4,6,12,14-hexaenyl)oxy]-N-butyl-acetamide (D) (150 mg, 0.44 mmol) was added to the mixture. The reaction was stirred at RT overnight. Then, 10 mL of water were added. A precipitate was formed and filtered then washed with water.

The product was purified by flash column chromatography (DCM/MeOH gradient) to give: N-butyl-2-[[2-[2-[2,3-dichloro-4-(2-methylenebutanoyl)phenoxy]acetyl]amino]-5-tricyclo[9.4.0.03,8]pentadeca-1(11),3(8),4,6,12,14-hexaenyl]oxy]acetamide (FIG. 28) (135 mg, 50% yield) as a white solid.

LCMS Calculated for $C_{34}H_{36}Cl_2N_2NaO_5$, 645.2, Observed [M+Na]$^+$645.3

1H NMR (80 MHz, DMSO-d6) δ 9.03 (d, J=7.7 Hz, 1H), 7.99 (t, J=5.6 Hz, 1H), 7.49-6.93 (m, 7H), 6.89-6.62 (m, 2H), 6.24 (d, J=7.7 Hz, 1H), 6.06 (s, 1H), 5.54 (s, 1H), 4.86 (s, 2H), 4.41 (s, 2H), 3.25-2.80 (m, 5H), 2.43-2.13 (m, 1H), 1.58-0.63 (m, 12H)

13C NMR (20 MHz, DMSO-d6) δ 195.1, 167.3, 165.5, 157.0, 155.6, 149.4, 140.0, 139.0, 138.6, 132.3, 131.6, 130.0, 129.3, 127.7, 127.4, 125.9, 121.1, 116.2, 111.9, 67.7, 67.0, 54.9, 37.9, 32.0, 31.6, 31.2, 22.9, 19.5, 13.6, 12.3

HRMS Calculated for $C_{34}H_{37}Cl_2N_2O_5$ ([M+H]$^+$) 623.2074, found 623.2070.

Synthesis of N-[6-[2-(butylamino)-2-oxo-ethoxy]-2-tricyclo[9.4.0.03,8]pentadeca-1(11),3(8),4,6,12,14-hexaenyl]-4-[4-(1-hydroxyethyl)-2-methoxy-5-nitro-phenoxy]butanamide (FIG. 29)

To a solution of 4-[4-(1-Hydroxyethyl)-2-methoxy-5-nitrophenoxy]butyric acid (159.3 mg, 0.53 mmol) in 2 mL of DMF at RT, were added HBTU (252.3, 0.67 mmol) then DIEA (153.5 μL, 0.89 mmol) successively. The reaction was stirred at RT for 30 min then 2-[(2-amino-6-tricyclo[9.4.0.03,8]pentadeca-1(11),3(8),4,6,12,14-hexaenyl)oxy]-N-butyl-acetamide (D) (150 mg, 0.44 mmol) was added to the mixture. The reaction was stirred at RT overnight. Then, 10 mL of water were added. A precipitate was formed and filtered then washed with water.

The product was purified by flash column chromatography (DCM/MeOH gradient) to give: N-[6-[2-(butylamino)-2-oxo-ethoxy]-2-tricyclo[9.4.0.03,8]pentadeca-1(11),3(8),4,6,12,14-hexaenyl]-4-[4-(1-hydroxyethyl)-2-methoxy-5-nitro-phenoxy]butanamide (FIG. 29): (118 mg, 43% yield) as a light yellow solid.

LCMS Calculated for $C_{34}H_{41}N_3O_8$, 619.2, Observed [M+Na]$^+$642.3

1H NMR (80 MHz, DMSO-d6) δ 8.89 (d, J=7.9 Hz, 1H), 8.14-7.78 (m, 1H), 7.53-7.08 (m, 7H), 6.81-6.56 (m, 2H), 6.29 (d, J=7.9 Hz, 1H), 5.58-5.39 (m, 1H), 5.39-5.10 (m, 1H), 4.39 (s, 2H), 4.11-3.83 (m, 5H), 3.25-2.96 (m, 6H), 2.42-2.14 (m, 2H), 2.11-1.82 (m, 2H), 1.37 (d, J=6.1 Hz, 7H), 0.95-0.72 (m, 3H)

13C NMR (20 MHz, DMSO-d6) δ 175.6, 170.1, 167.0, 156.5, 153.1, 145.9, 139.5, 138.5, 138.1, 137.7, 132.0, 129.5, 128.3, 126.8, 125.4, 115.8, 111.5, 108.7, 108.0, 67.9, 66.7, 63.5, 55.7, 37.5, 31.6, 31.2, 31.1, 30.8, 24.8, 24.4, 19.1, 13.3

HRMS Calculated for $C_{34}H_{42}N_3O_8$ ([M+H]$^+$) 620.2966, found 620.2965.

Note: the reported yields do not represent the chemical conversion yields. Only top purity fractions were isolated from chromatography (for activity and affinity tests).

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A sirtuin inhibiting compound and/or salt thereof is of Formula I:

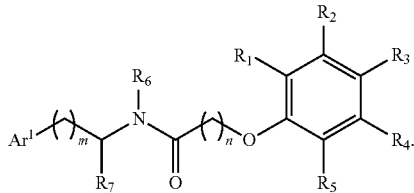

wherein Ar$^1$ is aryl or heteroaryl, R$_1$-R$_7$ are independently selected from the group consisting of hydrogen, alkyl, alkenyl, heteroalkyl, cycloalkyl, heterocycloalkyl, —C(O)R$_8$, alkoxy, halo, nitryl (—NO$_2$), and hydroxy, wherein the Ar$^1$, alkyl, alkenyl, heteroalkyl, cycloalkyl, heterocycloalkyl, aryl, heteroaryl are optionally substituted with one or more substituents selected from the group consisting of (C$_1$-C$_{10}$)-alkyl, (C$_1$-C$_{10}$)-alkenyl, alkoxy, halo, amine, and hydroxy; and wherein R$_8$ is selected from the group consisting of alkyl, alkenyl, and NR$_9$R$_{10}$, wherein R$_9$ and R$_{10}$ are independently selected from the group consisting of hydrogen, alkyl, and cycloalkyl; and wherein m and n are integers each having a value independently selected from 0 to 10.

2. The sirtuin inhibiting compound of claim 1, wherein R$_1$-R$_7$ are independently selected from the group consisting of hydrogen, alkyl, halo, and —C(O)R$_8$.

3. The sirtuin inhibiting compound of claim 1, wherein Formula I and/or salt thereof is:

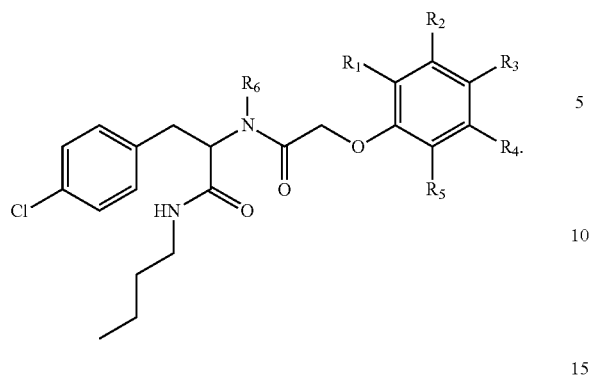
4. The sirtuin inhibiting compound of claim 1, wherein the compound is a Sirt3 inhibitor.
5. The sirtuin inhibiting compound of claim 1, wherein Formula I and/or salt thereof is:
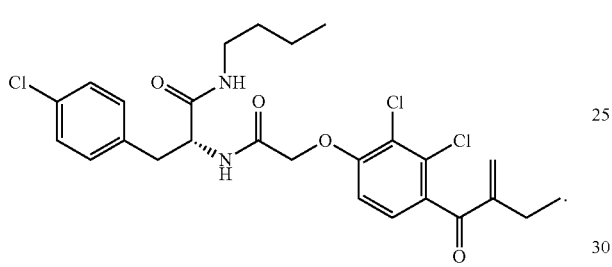
* * * * *